(12) United States Patent
Larkin

(10) Patent No.: US 7,283,221 B2
(45) Date of Patent: Oct. 16, 2007

(54) REFRACTOMETER CELL FOR BOTH ABSOLUTE AND DIFFERENTIAL REFRACTIVE INDEX MEASUREMENT OF FLUIDS

(75) Inventor: Michael I. Larkin, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 360 days.

(21) Appl. No.: 10/723,548

(22) Filed: Nov. 25, 2003

(65) Prior Publication Data

US 2005/0110982 A1    May 26, 2005

(51) Int. Cl.
*G01N 21/41* (2006.01)
(52) U.S. Cl. .................................................. 356/130
(58) Field of Classification Search ................ 356/133
See application file for complete search history.

(56) References Cited

U.S. PATENT DOCUMENTS

| | | | |
|---|---|---|---|
| 2,427,996 A | 9/1947 | Seaman | |
| 2,741,942 A | 4/1956 | Svensson | |
| 2,800,053 A | 7/1957 | Svensson | |
| 6,975,392 B2 * | 12/2005 | Larkin | 356/246 |

FOREIGN PATENT DOCUMENTS

EP            0682242 A1    11/1995

OTHER PUBLICATIONS

Copending U.S. Appl. No. 10/961,633.*

* cited by examiner

Primary Examiner—Gregory J. Toatley, Jr.
Assistant Examiner—Amanda H Merlino
(74) Attorney, Agent, or Firm—Philip J. Wyatt

(57) ABSTRACT

An improved cell for a walk-off refractometer is disclosed that permits measurement of the differential refractive index, DRI, between a sample fluid and a reference fluid. In addition, the new cell design permits the measurement of the refractive index, RI, of a fluid relative to the refractive index of the material comprising or surrounding the flow cell. Thus a single instrument may be used to measure separately the RI of a sample fluid and the DRI between a sample fluid and a reference fluid. The new flow cell contains two chambers, typical of a DRI instrument, but an asymmetric internal angle in either the sample or the reference chamber. By the provision of this unique structure, it is an objective of this invention to be able to measure the refractive index of a fluid relative to the refractive index of the material comprising the flow cell or relative to the medium surrounding the flow cell, either of which may be considered a measurement of the RI of the fluid. With the addition of mirror means, it is the further objective of this invention to improve its sensitivity. A further objective of the invention is to measure the asymmetric internal angle of the flow cell using well-characterized reference fluids.

8 Claims, 4 Drawing Sheets

REFRACTOMETER CELL FOR BOTH ABSOLUTE AND DIFFERENTIAL REFRACTIVE INDEX MEASUREMENT OF FLUIDS

BACKGROUND

The difference in refractive index between a sample and a reference material is called the differential refractive index, or DRI, and is a physical parameter of considerable importance. In liquid chromatography, the DRI between a sample liquid consisting of a mobile phase plus a solute and a reference liquid, which is the pure mobile phase, is often used as a determination of solute concentration. Another physical parameter of interest is the absolute refractive index, RI, of a fluid. In general chemistry, the RI is used to identify liquids, determine the purity of liquids, and to measure high concentrations of dissolved molecules such as sugar solutions. In light scattering measurements, the RI of the mobile phase is an important input parameter in determining the molar mass and size of molecules and particles.

To date there has been no one instrument which can measure both the DRI between a sample fluid and a reference fluid, and the RI of a fluid. A typical instrument for measuring the DRI only is a "walk-off" type differential refractometer. That instrument contains a transparent cell containing two fluid chambers, and having an angled transparent window separating the chambers. A beam of light passes into the cell, through one chamber, through the angled window separating the chambers, through the second chamber, and finally out of the cell, as pictured in FIG. 1. For the cell pictured, if the fluids in the two chambers have identical indices of refraction, then after exiting the cell, the transmitted beam of light travels in a path parallel to the incident beam. If the two fluids have different indices of refraction, then the transmitted beam of light travels at an angle different from the direction of the incident beam. The angle between the incident light beam and the transmitted light beam is, to first order, proportional to the difference in refractive index between the two liquids. The angular deflection of the light beam may be measured by a variety of well-established techniques, and so the DRI of one fluid relative to the other may be measured and reported. It is noted that the fluids are usually introduced into the respective chambers by connection means providing flows transverse to the planes shown. Each chamber contains means to introduce and remove fluids contained therein, usually on opposite sides of the chambers.

A very simple, though imprecise, instrument that may be used for the measurement of the RI of a fluid is comprised of a transparent cell with only one fluid chamber. The fluid chamber has at least one wall that is oriented with respect to the incoming beam, as shown in FIG. 2. A beam of light passes into the cell, through the fluid, and exits the cell via the angled face. The transmitted beam will have an angular deflection that depends upon the index of refraction of the fluid relative to the known RI of the air or medium surrounding the cell. Embodiments that are more precise would include the well-known Abbe refractometer. As with the DRI instrument, that angular deflection may be measured by a variety of well-established techniques, and so the RI of the fluid may be reported. Note that the chambers used in the structures of FIGS. 1 and 2 are defined generally in terms of right triangles.

BRIEF DESCRIPTION OF THE INVENTION

This invention allows one instrument to measure separately the RI of a sample fluid and the DRI between a sample fluid and a reference fluid. The invention is comprised of a new type of flow cell that contains two chambers, typical of a DRI instrument, but an asymmetric internal angle in either the sample or the reference chamber. By the provision of this unique structure, it is an objective of this invention to be able to measure the refractive index of a fluid relative to the refractive index of the material comprising the flow cell or relative to the medium surrounding the flow cell, either of which may be considered a measurement of the RI of the fluid. In general, the preferred embodiment of the flow cell of the invention would-be surrounded by air. An additional objective of the invention is to be able to measure the difference in refractive index of a sample fluid relative to that of a reference fluid. With the addition of mirror means, it is the further objective of this invention to improve its sensitivity. Another objective of this invention is to measure precisely the refractive index of the fluid-containing cells using well-characterized reference fluids. A further objective of the invention is to measure the asymmetric internal angle of the flow cell using well-characterized reference fluids.

DETAILED DESCRIPTION OF THE INVENTION

Figure 1:
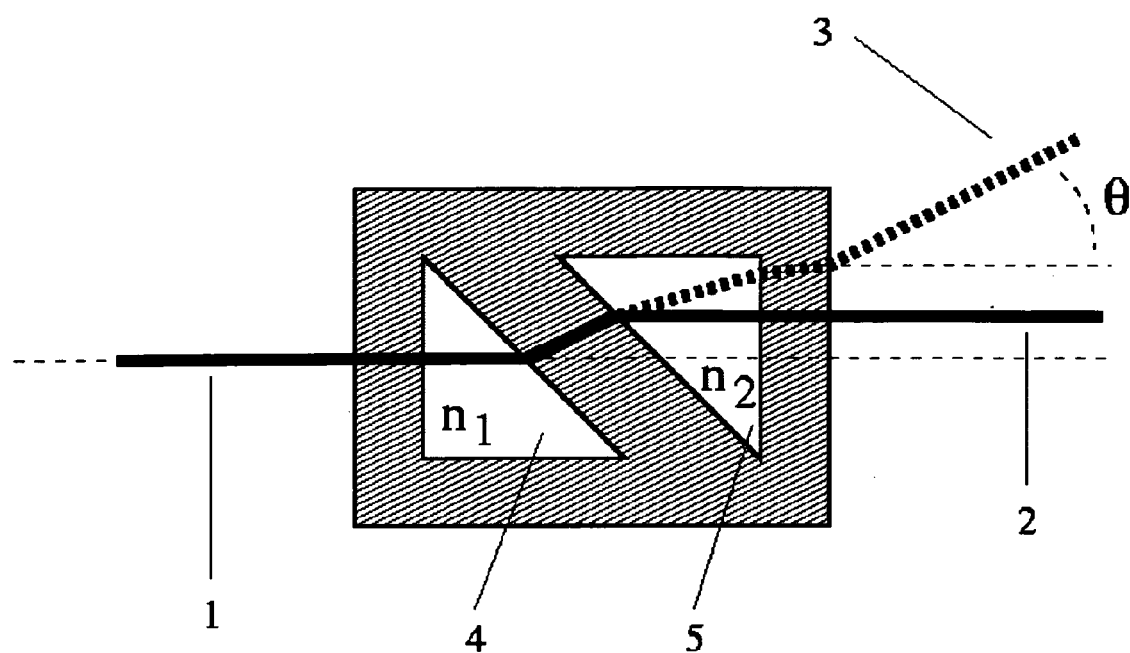
FIG. 1 illustrates a typical differential refractometer cell.
Figure 2:
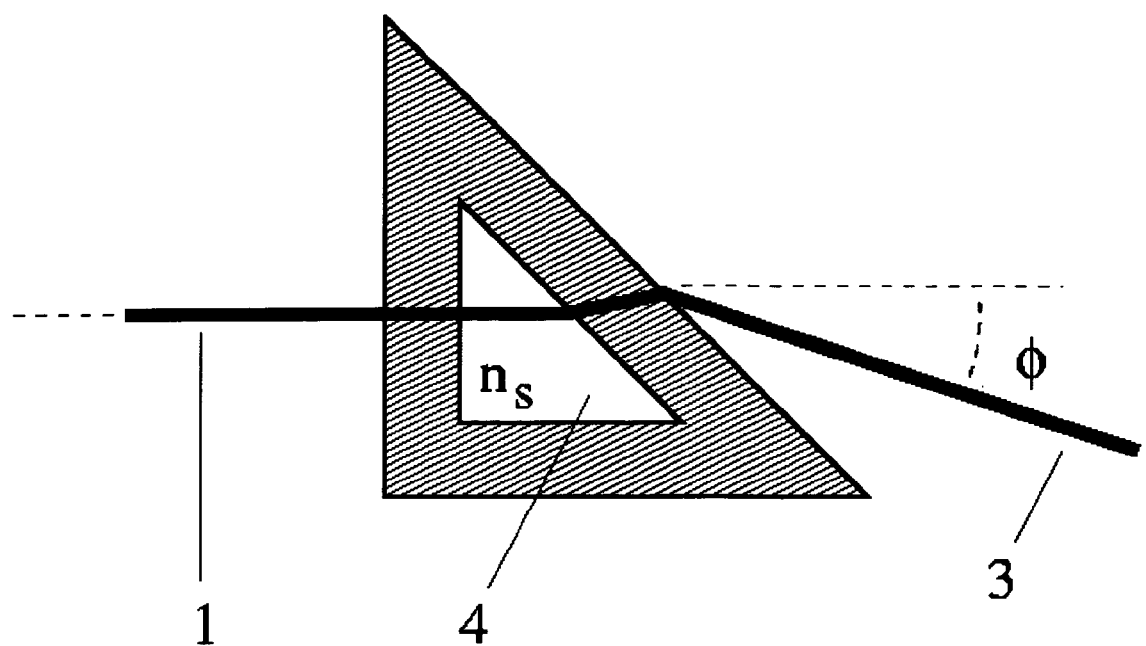
FIG. 2 illustrates an absolute refractometer cell.

For a typical DRI cell, as that pictured in FIG. 1, if chambers 4 and 5 are filled with identical fluids, $n_1=n_2$, the transmitted light beam 2 leaves the cell parallel to the direction of the incident beam 1. Note that the preferred embodiment of such DRI cells require that the fluid containing chambers 4 and 5 are similar triangles of right angle structure with their hypotenuses parallel to each other and their light transmitting sides parallel both to each other and to the external cell surfaces. When $n_1 \neq n_2$, the transmitted beam 3 now exits at some angle $\theta$ to the direction of the incident beam. In a simple absolute refractometer, as shown in FIG. 2, the light beam 1 is refracted as it passes through the sample chamber 4, thus emerging 3 at an angle $\phi$.

Figure 3:
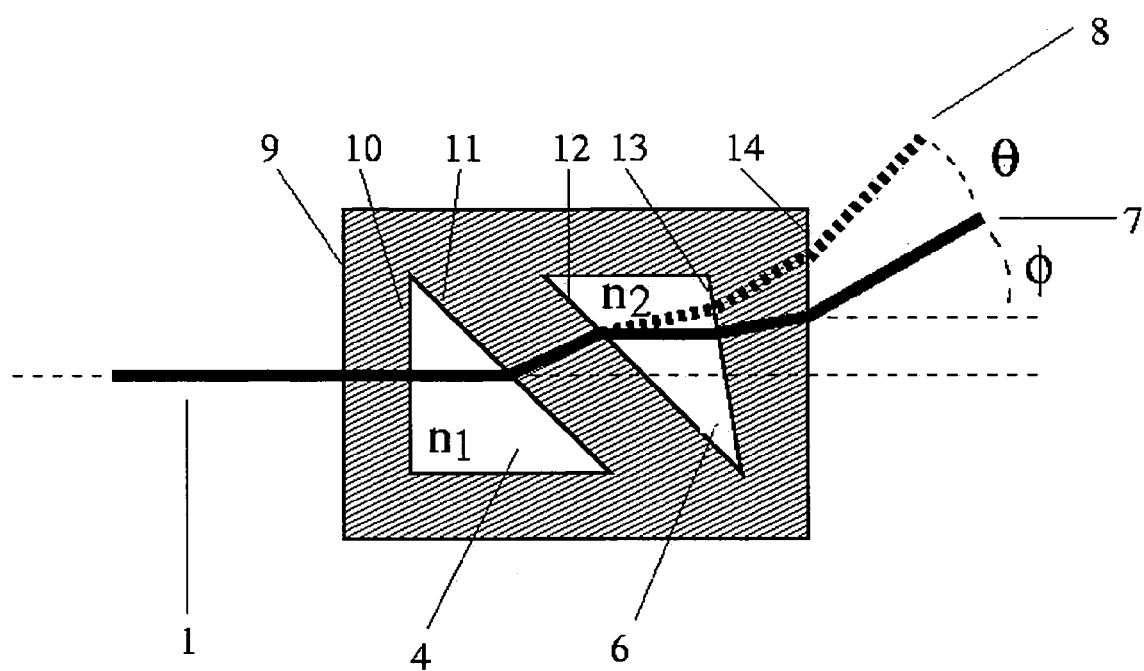
FIG. 3 illustrates the preferred embodiment of the inventive cell including an asymmetric internal angle in one of its chambers.

A preferred embodiment of the invention is shown in FIG. 3 wherein chamber 6 is no longer a right triangle, i.e. the surface 13 is not parallel to surface 10. Unlike the traditional configuration of FIG. 1 where both chambers form right triangles, the second chamber cavity is not a right triangle. For the case that both chambers are filled with the same liquid, i.e. $n_1=n_2$, the incident light beam 1 deflected by an angle $\phi$ which is a function of the refractive index difference between the fluid $n_2$ in chamber 6, the refractive index of the material comprising the cell, and the angular deviation of plane 13 from parallelity with plane 10. In general, the preferred embodiment of such chambers would be directed to structures surrounded by air. Theoretically, the surrounding media might be different than air, in which case the deflection angle measured would depend also upon the RI of the medium surrounding the cell. As such cases are easily represented by relations similar to those to be derived herewith, it will be assumed that the surrounding RI is equal to that of air, i.e. 1.0. Changing the RI of the surrounding medium is but an obvious variation of the simpler case of air discussed here. When $n_1=n_2$, the incident light beam 1 is deflected by an additional angle θ which is a function of the difference in refractive index between the fluid $n_1$ in chamber 4 and the fluid $n_2$ in chamber 6. Thus the light beam 8 exits the cell at some angle φ+θ. That additional angle θ becomes a measure of the DRI between $n_1$ and $n_2$.

The succesive surfaces through which the light beam passes are labeled in FIG. 3 as planes 9, 10, 11, 12, 13, and 14. As discussed above, an angular deviation φ due to the refractive index difference between a fluid in chamber 4 or 6 and the material comprising the cell results from nonparallelism of planes 10 and 13. If, as is shown in FIG. 3, planes 9, 10, and 14 are parallel to each other, but are not parallel to plane 13, then the angular deviation φ is due to the refractive index difference between a fluid in chamber 6 and the material comprising the cell. For the case of $n_1=n_2$, by measuring the angular deviation φ and knowing the refractive index of the material comprising the cell, we may report the RI of the identical fluids in chambers 4 and 6. If planes 9 and 10 are parallel to each other and planes 13 and 14 are parallel to each other, but planes 9 and 10 are not parallel to planes 13 and 14, then the angular deviation φ is due to the refractive index difference between the identical fluids and the surrounding medium, typically air. For the case of $n_1=n_2$, by measuring the angular deviation φ and knowing the refractive index of the medium surrounding the cell, typically air, we may report the RI of the identical fluids in chambers 4 and 6. Planes 11 and 12 are, in the preferred embodiment of this invention, always parallel as is the case for the conventional deflection type of DRI detector.

Figure 4:
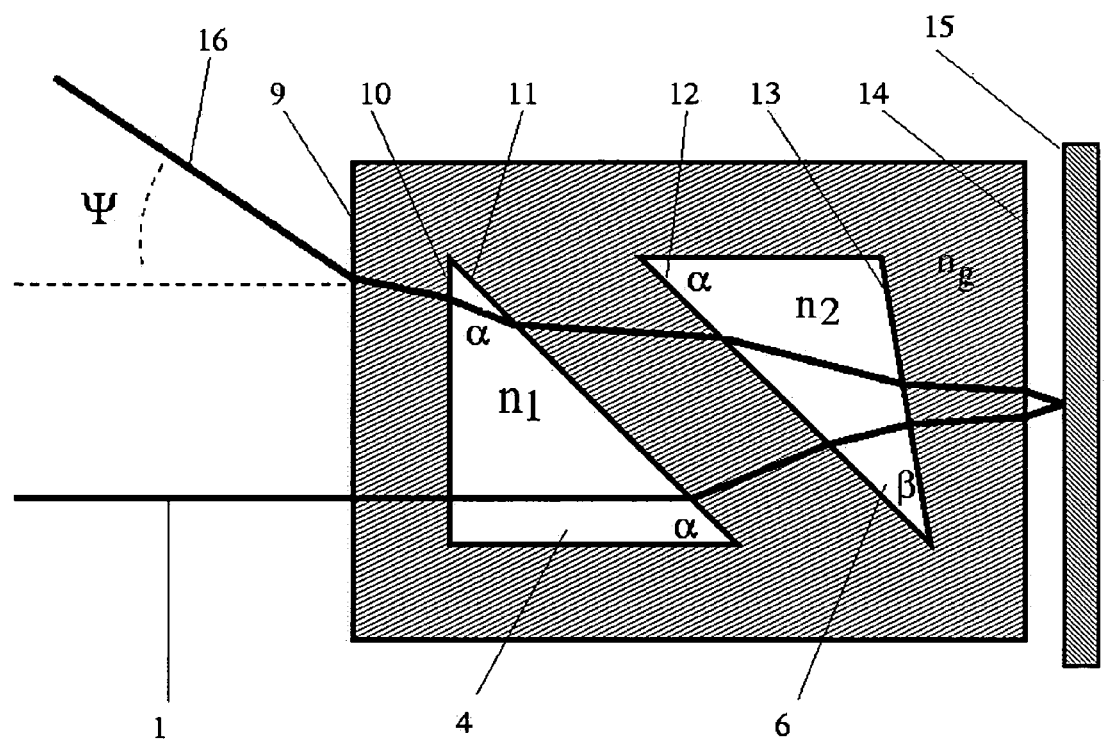
FIG. 4 illustrates the preferred embodiment of the invention whereby a reflective means has been added to the cell of FIG. 3.

The DRI cell pictured in FIG. 1 and the invention pictured in FIG. 3 show, for purposes of clarity, a light beam traversing the cell only once. In fact, most DRI instruments incorporate a mirror 15 as shown in FIG. 4 placed some distance behind the cell, causing the light beam to traverse the cell twice, thus doubling the angular deflection for a given DRI. Such mirrors will also double the angular deflection for a given RI. FIG. 4 shows the preferred embodiment of the invention with a light beam traversing the cell twice. In addition, angles of importance, α and β, have been labeled for further discussion and explanation in this description. Chamber 4 contains a fluid with index of refraction $n_1$, chamber 6 contains a fluid with index of refraction $n_2$, the cell material has index of refraction $n_g$, and the medium surrounding the cell has index of refraction $n_0$. Chamber 4 is an isosceles right triangle of base angle α. Chamber 6 has angles α, β<α, and π−β−α. As in FIG. 3, planes 9, 10, and 14 are parallel to each other and are not parallel to plane 13, and planes 11 and 12 are parallel to each other. The light beam 16 exits at an angle ψ with respect to the incoming beam 1. For the special case of $$\alpha = \frac{\pi}{4}$$

the angle of the outgoing beam 16 may be found to be, with the RI of the surrounding medium given by $n_0$, $$\sin(\psi) = \frac{n_1\sqrt{2}}{n_0 2}\left\{\left[1 - \left(\frac{n_2}{n_1}\right)^2\left(\sin^2(\beta)\left(1 - \left(\frac{n_g}{n_2}\right)^2 f^2\right) - \right.\right.\right. \tag{1}$$

$$\left. 2\sin(\beta)\cos(\beta)\left(\frac{n_g}{n_2}\right)f\left(1 - \left(\frac{n_g}{n_2}\right)^2 f^2\right)^{\frac{1}{2}} + \cos^2(\beta)\left(\frac{n_g}{n_2}\right)^2 f^2\right)\right]^{\frac{1}{2}} - $$

$$\left. \left(\frac{n_2}{n_1}\right)\left[\sin(\beta)\left(1 - \left(\frac{n_g}{n_2}\right)^2 f^2\right)^{\frac{1}{2}} - \cos(\beta)\left(\frac{n_g}{n_2}\right)f\right]\right\}$$

with $$f = \sin(2\beta)g - \cos(2\beta)(1 - g^2)^{\frac{1}{2}}$$

and $$g = \left(\frac{n_2}{n_g}\right)\left\{\cos(\beta)\frac{n_1\sqrt{2}}{n_2 2} - \sin(\beta)\left[1 - \left(\frac{n_1}{n_2}\right)^2 \frac{1}{2}\right]^{\frac{1}{2}}\right\}.$$

The angle β may be determined directly from measurement of the deflection angle ψ after filling both chambers with the same fluid whose refractive index $n_1$ is known at the wavelength $\lambda_0$ of the incident light beam. In this event, setting $n_1=n_2$, Eq. (1) simplifies to $$\sin(\psi) = \frac{n_1\sqrt{2}}{2}\left\{\left[1 - \left(\sin^2(\beta)\left(1 - \left(\frac{n_g}{n_1}\right)^2 f^2\right) - \right.\right.\right. \tag{2}$$

$$\left. 2\sin(\beta)\cos(\beta)\left(\frac{n_g}{n_1}\right)f\left(1 - \left(\frac{n_g}{n_1}\right)^2 f^2\right)^{\frac{1}{2}} + \cos^2(\beta)\left(\frac{n_g}{n_1}\right)^2 f^2\right)\right]^{\frac{1}{2}} - $$

$$\left. \left(\frac{n_2}{n_1}\right)\left[\sin(\beta)\left(1 - \left(\frac{n_g}{n_1}\right)^2 f^2\right)^{\frac{1}{2}} - \cos(\beta)\left(\frac{n_g}{n_1}\right)f\right]\right\}$$

where $$g = \left(\frac{n_1}{n_g}\right)\{\cos(\beta) - \sin(\beta)\}\frac{\sqrt{2}}{2}.$$

In the event the cell refractive index $n_g$ is also unknown, it is easily determined by using two reference fluids whose two corresponding refractive indices are $n_1$ and $n_2$, respectively. In this event, one fills both chambers first with the solution of known refractive index $n_1$ and then measures deflection angle ψ per Eq. (2). Next one fills both chambers with the solution of known refractive index $n_2$ and then measures the new deflection angle ψ' per Eq. (2), with $n_1$ replaced by $n_2$ and ψ by ψ'. The two unknowns β and $n_g$ may then be determined from the relations of Eq. (2) and the two aforementioned measurements.

Assuming a reference fluid in chamber 6 and a sample fluid in chamber 4, we may expand Eq. 1 making the substitution $n_1=n_2+\Delta n$. Assuming also that $n_0=1$, then to first order in $$\beta - \frac{\pi}{4}$$

and to second order in $\Delta n$, Eq. (1) may be written as:

$$\sin(\psi) = 2\Delta n\left\{1 + \left(1 - \frac{n_g}{n_2}\right)\left(\beta - \frac{\pi}{4}\right)\right\} + \qquad (3)$$

$$2(n_g - n_2)\left(\beta - \frac{\pi}{4}\right) + \Delta n^2\left\{\left(11\frac{n_g}{n_2^2} - \frac{1}{n_g} - \frac{10}{n_2}\right)\left(\beta - \frac{\pi}{4}\right) - \frac{1}{n_2}\right\}.$$

For $\Delta n=0$ (same fluid in both the sample and reference cells) the angle $\psi$ of the outgoing beam 16 is proportional to the difference between the indices of the fluid, $n_2$, and the cell material, $n_g$, with a proportionality constant of $$2\left(\beta - \frac{\pi}{4}\right).$$

If the index $n_g$ and angle $\beta$ are known, then by measuring $\sin(\psi)$ we may calculate $n_2$, the absolute refractive index of the fluid. If the cell material refractive index $n_g$ and angle $\beta$ are unknown, and at least two different fluids are available with known refractive indices, then as described above, by measuring $\sin(\psi)$ as a function of $n_1=n_2=n$, we may determine experimentally the cell material refractive index $n_g$ and angle $\beta$. For a given $n_2$ we then may change the index of refraction of the sample fluid producing a nonzero $\Delta n$. The outgoing beam will have a change in $\sin(\psi)$ which is to first order proportional to $\Delta n$. Finally, by measuring the change in $\sin(\psi)$, we may calculate $\Delta n$.

It is not necessary for the reference liquid to be contained in chamber 6. If instead of assuming that chamber 6 contains the reference fluid, we assume that chamber 4 contains the reference fluid, we may expand Eq. (1) making the substitution $n_2=n_1+\Delta n$. Assuming $n_0=1$, to first order in $$\beta - \frac{\pi}{4}$$

and to second order in $\Delta n$, Eq. (1) becomes:

$$\sin(\psi) = -2\Delta n\left\{1 + \left(1 - \frac{n_g}{n_1}\right)\left(\beta - \frac{\pi}{4}\right)\right\} + \qquad (4)$$

$$2(n_g - n_1)\left(\beta - \frac{\pi}{4}\right) -$$

$$\Delta n^2\left\{\left(-9\frac{n_g}{n_1^2} + \frac{1}{n_g} + \frac{10}{n_1}\right)\left(\beta - \frac{\pi}{4}\right) + \frac{1}{n_1}\right\}.$$

As with the previous expansion, the DRI and RI for the fluids may be separately determined, or with at least two fluids of known refractive index, we may determine the cell material refractive index $n_g$ and angle $\beta$.

Equation (1) and its subsequent expansions are based upon the specific geometry of FIG. 4. It will be clear to those skilled in the art of refractometry that the dRI and fluid RI may be determined separately for any case of nonparallelism of planes 10 and 13, and/or planes 11 and 12. It will be clear also to those skilled in the art of refractometry that by varying the angles of the external planes 9 and 14 it is possible to reference the RI of the fluid to the refractive index of the material comprising the cell, or to the refractive index of the medium surrounding the cell. As long as at least one of the plane pairs 10 and 13 or 11 and 12 are not parallel, the cell may be used to determine both the RI of an unknown fluid as well as the DRI between two different fluids such as a solvent and a solution in which a solute is dissolved in the solvent. Obviously, if more than a single plane of each of the afore-referenced pairs is not parallel, that type of cell will also represent also another embodiment of my invention. For the case of such additional non-parallel surfaces, it must be emphasized that more generalized relations than indicated by Eq. (1) et seq. are easily derived. The associated internal angles of each such surface must be known or determined before my invention be applied. This will require a plurality of fluids whose RI values are known to derive these angles by refraction measurements such as described herein.

Key to the RI determinations that may be achieved by the preferred embodiment of the inventive methods described herewith is the solution of Eq. (1) for the variety of conditions that may be appropriate to the desire of the instrument user. For the practical ranges of the refractive indices of sample and reference fluids, the approximations of Eq. (3) or Eq. (4) will suffice to yield the RI of unknown fluids and/or the DRI of a sample fluid relative to a reference fluid to sufficient precision for both chromatographic and stand-alone purposes. In the event that additional precision is required, it become a simple task to solve Eq. (1) directly by, for example, Newton's method using the approximations of Eq. (3) or Eq. (4) as a starting point.

In the description of the multifunction refractometer that I have discussed above, I have emphasized the numerous variations on my invention that will be clearly obvious to those skilled in the art of refractometry. Such variations are but obvious extentions of the invention I claim as follows:

The invention claimed is:

1. An improved refractometer cell constructed of a transparent material of refractive index $n_g$ and comprising
   A. a first exterior surface (9) and a second exterior surface (14), said first and second exterior surfaces (9, 14) permitting a light beam (1) to pass therethrough so as to enter and exit, respectively, the refractometer cell, and
   B. a pair of fluid-containing chambers (4, 6) through which said light beam passes, said chambers (4, 6)
      1) each forming a cavity which contains at least two plane, non-parallel surfaces (10, 11 and 12, 13);
      2) are separated by a transparent window therebetween;
      3) contain fluids of refractive index $n_1$ and $n_2$ respectively, and;
      4) are characterized in that said chambers comprise entrance and exit beam-passing plane surfaces (10, 11, 12, 13), at least one of which has no other internal beam-passing surface parallel thereto.

2. A method to determine the angle $\beta$ of the second chamber (6) of the improved refractometer cell (9) of claim 1 when the refractive index $n_g$ of the transparent material of said cell is known, comprising the steps of
   A. preparing a fluid whose refractive index $n_1$ is known;
   B. filling both chambers of said refractometer cell with said fluid;

C. illuminating the cell with a fine beam of light whose vacuum wavelength $\lambda_0$ is known, D. measuring the angle of deflection $\psi$ of the transmitted beam E. calculating $\beta$ from the relation $$\sin(\psi) = \frac{n_1\sqrt{2}}{2}\left\{\left[\frac{1 - \left(\sin^2(\beta)\left(1 - \left(\frac{n_g}{n_1}\right)^2 f^2\right) - 2\sin(\beta)\cos(\beta)\left(\frac{n_g}{n_1}\right)\right)}{f\left(1 - \left(\frac{n_g}{n_1}\right)^2 f^2\right)^{\frac{1}{2}} + \cos^2(\beta)\left(\frac{n_g}{n_1}\right)^2 f^2}\right]^{\frac{1}{2}} - \left(\frac{n_2}{n_1}\right)\left[\sin(\beta)\left(1 - \left(\frac{n_g}{n_1}\right)^2 f^2\right)^{\frac{1}{2}} - \cos(\beta)\left(\frac{n_g}{n_1}\right)f\right]\right\}$$

where $$f = \sin(2\beta)g - \cos(2\beta)(1-g^2)^{\frac{1}{2}} \text{ and } g = \left(\frac{n_1}{n_g}\right)\{\cos(\beta) - \sin(\beta)\}\frac{\sqrt{2}}{2}.$$

3. The method of claim 2 for the case when $\beta \approx 45°$ and $n_g$ is known and said angle $\beta$ is determined from $$\beta = \frac{\sin\psi}{2(n_g - n_1)} + \frac{\pi}{4}$$

where said measured deflection angle is $\psi$.

4. The improved refractometer cell of claim 1 further incorporating mirror means (15) adjacent and parallel to said second exterior surface (14) causing the beam transmitted therethrough to be reflected back therefrom through said cell and exiting at said first exterior surface (9), where its angular deviation relative to the direction of said incident light beam (1) may be measured thereat.

5. The improved refractometer cell of claim 1 wherein the sides transverse to the incident beam of each chamber (4, 6) form a triangle.

6. The improved refractometer cell of claim 5 wherein said first chamber (4) forms an isosceles right triangle of 45° base angles ($\alpha$), said second chamber (6) forms a triangle with one 45° base angle ($\alpha$) and a second angle ($\beta$) less than 45° yielding a third angle greater than a right angle, and the hypotenuse (11) of the isosceles right triangle of said first chamber (4) is parallel to the longest side (12) of the triangle of said second chamber (6).

7. A method to measure the refractive index of a fluid, n, using the improved refractometer cell of claim 1 comprising the steps of A. filling both chambers of said cell with a fluid of known refractive index;

B. passing a fine beam of light therethrough;

C. measuring the deflection angle $\psi'$ of the emerging beam;

D. filling both chambers of said cell with said fluid whose said refractive index value n is to be measured;

E. measuring the deflection angle $\psi$ of the emerging beam;

F. calculating said refractive index value n from said measured values of $\psi'$ and $\psi$.

8. A method to measure the refractive index difference, $\Delta n$, of two fluids of refractive index $n_0$ and $n_0 + \Delta n$, respectively, using the improved refractometer cell of claim 1 comprising the steps of A. filling both chambers of said cell with a reference fluid of refractive index $n_0$;

B. passing a fine beam of light therethrough;

C. measuring the deflection angle $\psi'$ of the beam emerging therefrom;

D. replacing said reference fluid in one of said chambers of said cell with said second fluid of refractive index $n_0 + \Delta n$;

E. measuring the deflection angle $\psi$ of the emerging beam;

F. calculating said refractive index value difference $\Delta n$ between said two fluids from said measured values of $\psi'$ and $\psi$.

* * * * *